US005747260A

United States Patent [19]

Roberts et al.

[11] Patent Number: 5,747,260
[45] Date of Patent: May 5, 1998

[54] METHOD OF PROGNOSING CHRONIC NEURODEGENERATIVE PATHOLOGY FOLLOWING A HEAD INJURY

[75] Inventors: Gareth Wyn Roberts, Harlow, England; David Ian Graham; James Alan Ramsey Nicoll, both of Glasgow, Great Britain

[73] Assignee: SmithKline Beecham p.l.c., Brentford, England

[21] Appl. No.: 776,356

[22] PCT Filed: Jul. 13, 1995

[86] PCT No.: PCT/EP95/02828

§ 371 Date: Feb. 25, 1997

§ 102(e) Date: Feb. 25, 1997

[87] PCT Pub. No.: WO96/03656

PCT Pub. Date: Feb. 8, 1996

[30] Foreign Application Priority Data

Jul. 27, 1994 [GB] United Kingdom ............... 9415073

[51] Int. Cl.[6] .................. C12Q 1/68; C12P 19/34; C07H 21/02; C07H 21/04
[52] U.S. Cl. ................ 435/6; 435/7.1; 435/7.2; 435/7.9; 435/91.2; 530/388.2; 436/500; 424/88; 536/23.1; 536/24.3; 536/24.33
[58] Field of Search ................ 435/6, 7.1–7.9, 435/91.2; 530/388.2; 436/500; 424/88; 536/23.1, 24.3, 24.33

[56] References Cited

FOREIGN PATENT DOCUMENTS

WO 94/09155  4/1994  WIPO .

OTHER PUBLICATIONS

Vanderputten. Dissertation Abstracts International. 1 Oct. 1993, vol. 54, No. 4, *Identification and characterization of apolipoprotein E in human neurodegeneration*, .

Roberts et al. Journal of Neurology, Neurosurgery and Psychiatry. Jan. 1994, vol. 57, pp. 419–425.

Nicoll et al. Nature Medicine, 1995, vol. 1 No. 2, pp. 135–137.

*Primary Examiner*—W. Gary Jones
*Assistant Examiner*—Dianne Rees
*Attorney, Agent, or Firm*—James M. Kanagy; Stephen Venetianer; Edward T. Lentz

[57] ABSTRACT

A method of prognosing a head-injured subject or a subject who may be at risk of sustaining a head injury for the likelihood that a head injury might give rise to a chronic neurodegenerative pathology which could result in neuropsychological, psychiatric or neurological deficits, the method comprising detecting the presence or absence of ApoE isoforms or of DNA encoding ApoE isoforms in the subject.

5 Claims, No Drawings

METHOD OF PROGNOSING CHRONIC NEURODEGENERATIVE PATHOLOGY FOLLOWING A HEAD INJURY

The present invention relates to methods of prognosing the likelihood of neurodegenerative pathology and dementia in head-injured patients.

Accidental or non-accidental head injuries are common events. The precise number of patients suffering a head injury are difficult to calculate exactly since the methods of defining and counting cases varies from country to country. However the relevant figures for the UK serve as a useful guide to the extent of the problem. In the UK some 300 persons per 100,000 of the population are admitted to hospital each year as a result of head injury. Of these patients 9 per 100,000 will die as a direct result of the severity of their injuries. Outcome surveys in the USA indicate that for every 100 head injury survivors up to 5 remain in a coma, up to 15 are still severly disabled six months after injury, 20 have minor psychiatric or psychological problems and the remaining 60 will make a good recovery. These figures give rise to an estimated population of some 500,000 persons in the USA who have a persisting handicap as a result of trauma related head injury. The social and economic cost of dealing with the after effects of such injuries is large[1,2,3,4].

The cause of this problem is the brain damage that occurs in up to 30% of patients who are admitted to hospital with a head injury[4]. The damage arises from the physical effects of the trauma (such as swelling, herniation, haemorrhage, global or focal damage or compromise of the vascular supply, contusion, cranial and peripheral nerve damage, axonal injury and embolism[3,4,5,6]) and also from the neurochemical consequences of the ischaemia which invariably accompanies physical brain damage[3,4,5,6]. Such injuries and subsequent damage are often widespread and can involve regions of the spinal cord, cranial and peripheral nerves in addition to the brain[1,3,4].

In addition the brain damage caused by head injury also produces the risk of subsequent psychiatric and neurologic complications including epilepsy and chronic neurodegenerative states (eg dementia pugilistica or punch drunk syndrome)[3,4,5,6,7,8,9,10,11].

The extent of brain damage caused by a head injury can vary markedly from patient to patient Thus, the likelihood and degree of sustaining pathological brain damage in the immediate aftermath of the trauma and the risk of subsequent chronic neurodegeneration leading to epilepsy or a dementing condition vary also.

The pathophysiology of head injury has been investigated in an effort to determine the molecular mechanisms which enable the acute triggering event of a head injury to be transformed into a chronic neurodegenerative pathological process[12,13,14,15].

Head-injured patients show increased levels of β amyloid precursor protein immunoreactivity[14] and some 30% of head injured patients have evidence of β amyloid protein deposition[15]. This deposition can occur within days of a single head injury. The eventual consequence of substantial numbers of β amyloid deposits is the emergence of a clinical syndrome of cognitive decline and increasing dementia[3,8]. Such deposits have been shown to be present in a number of dementing syndromes and these include Alzheimer's disease, cortical Lewy body disease, Parkinson's disease and the Alzheimer-type disease in patients with Down's syndrome[3]. In addition β amyloid deposits are present in the brains of patients with vascular and cerebrovascular disease and these latter conditions can predispose or contribute to the above diseases[3].

Recently, the apolipoprotein E (ApoE) genotype has been shown to be an important determinant in the etiology of AD[16-23] with the presence and number of E4 alleles being associated with increased risk and earlier ages of onset of disease in both familial cases linked to chromosome 19 and sporadic cases. The presence of E2 alleles has been claimed to decrease the risk (be 'protective') of late onset Alzheimer disease[18,19,24]. This inference is based on the increased frequency of ApoE4 alleles in patients known to have Alzheimer's disease and the later age at onset of disease in patients with the ApoE2/3 genotype compared to the ApoE4/4 genotype[24,25].

Such general 'protective' effects of the E2 allele have been reported previously in the general population with respect to heart disease[26,27].

The exact role of ApoE in the pathology of Alzheimer-type disease is uncertain. ApoE is co-localised with β amyloid within plaques in the central nervous system (CNS)[34] and has been shown to bind to β amyloid in vitro[35,36,37] and to tau proteins[28]. This has led to the hypothesis that ApoE/tau interactions are critical in the pathophysiology of tangle formation and thus central to the process of Alzheimer-type diseases[28]. However, neither parkinson dementia complex of Guam nor aged Down's syndrome patients show increased levels of ApoE4 alleles despite the presence of large numbers of tangles in the CNS[29,30]. As such the role of ApoE in the pathology of Alzheimer type dementia remains obscure.

The exact relationship of various environmental factors like head injury to subsequent degenerative conditions like Alzheimer's disease is uncertain. Although epidemiological studies provide some evidence for a link[9] the reason for the susceptibility to a chronic degenerative condition following head injury in some patients[8,9,10,11,15] is unknown at present.

Methods of diagnosing or prognosing Alzheimer's disease have been described (WO 94/09155) based upon detecting (directly or indirectly) the presence or absence of an apolipoprotein E type 4 (ApoE4) isoform in the subject. The ApoE alleles E2, E3 and E4 are described in the literature[31,32].

It has now been found that the frequency of ApoE4 alleles in those individuals with β amyloid deposition following head injury is of the same high order as that seen in Alzheimer's disease, while in those head injured individuals without β amyloid deposition, the ApoE4 allele frequency is similar to that in non-Alzheimer's disease controls.

This evidence provides the first explanation for the susceptibility of some patients to a chronic neurodegenerative pathological process following the types of brain damage (eg axonal shearing, swelling, herniation, hemorrhage and ischaemia) caused by a head injury.

The present invention therefore provides a method of prognosing in a head-injured subject or a subject who may be at risk of sustaining a head injury for the likelihood that a head injury might give rise to a chronic neurodegenerative pathology which could result in neuropsychological, psychiatric or neurological deficits, the method comprising detecting the presence or absence of ApoE isoforms or of DNA encoding ApoE isoforms in the subject.

The step of detecting the presence or absence of ApoE isoforms or of DNA encoding such isoforms may be carried out either directly or indirectly by any suitable means, such as by techniques well known in the art, and is preferably carried out ex vivo (eg by means of the method described[33,38]). All generally involve the step of collecting a sample of biological material containing either DNA or ApoE from the subject, and then detecting which isoforms the subject possesses from that sample. For example, the detecting step may be carried out by collecting an ApoE sample from the subject (for example, from cerebrospinal fluid, or any other fluid or tissue containing ApoE), and then determining the presence or absence of an ApoE isoform in the ApoE sample (eg, by isoelectric focusing or immunoassay). In the alternative, the detecting step may be carried out by collecting a biological sample containing DNA from the subject, and then determining the presence or absence of DNA encoding an ApoE isoform in the biological sample. Any biological sample which contains the DNA of that subject may be employed, including tissue samples and blood samples, with blood cells being a particularly convenient source. Determining the presence or absence of DNA encoding an ApoE isoform may be carried out with an oligonucleotide probe labelled with a suitable detectable group, or by means of an amplification reaction such as a polymerase chain reaction or ligase chain reaction (the product of which amplification reaction may then be detected with a labelled oligonucleotide probe). Further, the detecting step may include the step of detecting whether the subject is heterozygous or homozygous for the gene encoding an ApoE isoform. Numerous different oligonucleotide probe assay formats are known which may be employed to carry out the present invention. Suitable examples of techniques and strategies for detecting the ApoE isoforms and encoding DNA are described in WO 94/09155.

It will be readily appreciated that the detecting steps may be carried out directly or indirectly. Thus, for example, any of the techniques described above for detecting ApoE2 may instead be used to detect ApoE3 and ApoE4. If either ApoE4 or ApoE3 is also detected in the subject, then it is determined that the subject is not homozygous for ApoE2; and if both ApoE4 and ApoE3 are detected in the subject, then it is determined that the subject is neither homozygous nor heterozygous for ApoE2.

The present invention has utility in enabling improvements in the clinical prognosis of patients who have suffered a degree of brain damage following a head injury.

In addition the invention has utility in allowing definition of the degree of risk in individuals who may be at risk of sustaining a head injury through social or professional activities (eg amateur and professional boxers, divers and other sportsmen such as rugby players, mountain climbers, judo players etc) or through elective medical procedures known to be associated with increased risk of brain damage (eg cardiac bypass operations, carotid endardectomy, brain surgery etc).

The method of the invention may thus be used to determine the degree of risk in participating in sporting events or clinical procedures. Such prognostications will have considerable utility in the design, planning and implementation of clinical care for patients in the event of a head injury and in the appropriate therapeutic intervention or the degree of hospital/social intervention or support required by a patient deemed to be at greater risk of a neurodegenerative disorder or in the design and analysis of clinical trials to determine the efficacy of therapeutic agents in the treatment of the types of brain damage which occur following head injury.

EXAMPLE

Method

Individuals surviving for less than two weeks following a severe head injury were selected from the Glasgow head injury database[4]. Most of the injuries were due to road traffic accidents or falls. Immunostaining for β-amyloid protein (β-AP) and Apolipoprotein E (ApoE) genotyping[38] were performed by standard methods.

Data

Deposits of β-amyloid protein resembling diffuse plaques were present in the cerebral cortex in 23 out of 90 (26%) individuals (Table 1). The ApoE-E4 allele frequency in those individuals with deposition of β-AP was 0.52 (Table 2a) compared with 0.16 for those individuals without β-AP deposition (chi square 23.013: 1 df, p<0.00001). This is similar to the previously published ApoE-E4 frequencies in individuals with Alzheimer's disease and age-matched control, respectively. Age stratification of the data indicates that the relationship between ApoE-E4 and β-AP deposition holds for those head-injured patients under 60 years of age (Table 2b). The proportion of head-injured individuals with β-AP deposition for each ApoE genotype is shown in Table 3. The proportion of head-injured individuals with β-AP deposition increased with the number of ApoE-E4 alleles (Table 4) from 10% for those without an E4 allele, to 35% for those with one E4 allele, to 100% (6 out of 6) for the relatively rare E4 homozygote. Within the group of patients with β-AP deposits, when the plaque density was assessed semi-quantitatively (sparse, moderate, frequent) it was found to be related to ApoE-E4 gene dose (Table 5).

TABLE 1

Descriptive statistics for head-injured individuals with (β-AP+) and without (β-AP−) β-AP deposition

|  | B-AP+ | B-AP− |
|---|---|---|
| Number | 23 | 67 |
| Age (years) |  |  |
| mean ± SD | 52 ± 19 | 28 ± 18 |
| range | 14–75 | 0.15–79 |
| Survival following head injury (days) |  |  |
| mean ± SD | 3.3 ± 4 | 2.9 ± 3 |
| range | <1–13 | <1–13 |

TABLE 2

ApoE allele frequencies in head-injured individuals with β-AP deposition (β-AP+) and without (β-AP−)

| ApoE allele | β-AP+ | β-AP− |
|---|---|---|
| a. All head-injured patients | | |
| E2 | 1/46 (0.02) | 14/134 (0.1) |
| E3 | 21/46 (0.46) | 98/134 (0.73) |
| *E4 | 24/46 (0.52) | 22/134 (0.16) |
| b. Head-injured patients under 60 years of age | | |
| **E4 | 14/28 (0.5) | 22/126 (0.16) |

*$\chi^2$ = 23.013, 1 df, p <0.00001
**$\chi^2$ = 13.542, 1 DF, P <0.001

TABLE 3

Proportion of individuals with deposition of β-AP (β-AP+) according to ApoE genotype

| ApoE genotype | Proportion of individuals β-AP+ | Percentage |
|---|---|---|
| 2/2 | 0/2 | 0% |
| 2/3 | 0/7 | 0% |
| 3/3 | 5/41 | 12% |
| 2/4 | 1/4 | 25% |
| 3/4 | 11/30 | 37% |
| 4/4 | 6/6 | 100% |

TABLE 4

Proportion of individuals with deposition of β-AP (β-AP+) according to the ApoE-E4 gene dose.

| ApoE-E4 gene dose | Proportion of β-AP+ individuals | Percentage |
|---|---|---|
| 0 | 5/50 | 10% |
| 1 | 12/34 | 35% |
| 2 | 6/6 | 100% |

$\chi^2$ for trend = 22.85, 1 df, p <0.001

TABLE 5

β-AP plaque numbers according to the ApoE-E4 gene dose.

| ApoE-E4 gene dose | Proportion of head-injured patients with 'frequent' β-AP plaques | Percentage |
|---|---|---|
| 0 | 0/5 | 0% |
| 1 | 4/1212 | 33% |
| 2 | 4/6 | 66% |

$\chi^2$ for trend p = 0.02

References

1. D W Anderson, R L McLaurin. Report on the national head and spinal cord injury survey conducted for the National Institute of neurological and Communicative Disorder & Stroke. Jour of Neurosurg, 1980, 53: Suppl. S1–S43.

2. W F Caveness. Incidence of craniocerebral trauma in the United States in 1976 with trend from 1970 to 1975. In: Thompson R. Green J R (ed). Advances in neurology, Vol. 22, Complications of nervoussystem trauma. Raven Press, New York, 1979, p1.

3. Roberts G W, Leigh P N and Weinberger D. Neuropsychiatric Disorders. Gower Medical press. London 1993.

4. J H Adams. Head injury. In: J H Adams & L W Duchen (Eds.), Greenfield Neuropathology, 5th edition 1992. Edward Arnold, London, Melbourne, Auckland. p106–152.

5. J H Adams, D. Doyle, I Ford, T A Genarelli, D I Graham & D R McLellan. Diffuse axonal injury in head injury: definitions, diagnosis and grading. Histopathology 1989, 15: 49–59.

6. Anon editorial. Head trauma victims in the UK: undeservedly underserved. Lancet 1990, 335 886–887.

7. J A N Corsellis, C J Bruton & D Freeman-Browne. The aftermath of boxing. Psychol Med 1973, 3: 270–273.

8. W A Lishman. Senile dementias, presenile dementias and pseudodementias. In: Organic Psychiatry, 2nd edition, Blackwell Scientific, London, Oxford 1987.

9. J A Mortimer, C M Van Duijn, & V Chandra. Head trauma as a risk factor for Alzheimer's disease: a collaborative re-analysis of case-control studies. Int. J Epidemiol 1991, 20: S28.

10. A J Roberts. Brain Damage in Boxers. Pitman, London (1969).

11. R Rudelli, J O Strom & P T Welch. Post-traumatic premature Alzheimer's disease: neuropathologic findings and pathogenic considerations. Arch Neurol, 1982, 39: 570–575.

12. G W Roberts. Immunocytochemistry of neurofibrillary tangles in dementia pugilistica and Alzheimer's disease: evidence for common genesis. Lancet, 1988, 2(8626–8627): 1456–1458.

13. G W Roberts, D Allsop & C J Bruton. The occult aftermath of boxing. J Neurol Neurosurg Psychiatry, 1990a, 53: 373–378.

14. S M Gentleman, D I Graham and G W Roberts. Molecular pathology of head trauma: altered βAPP metabolism and the etiology of Alzheimer's disease. Progress in Brain Research, 1993 96: 237–246.

15. G W Roberts, S M Gentleman, A Lynch, L Murray, M Landon & D I Graham. β-amyloid protein deposition in the brain following severe head injury: implications for the pathogenesis of Alzheimer's disease. Journal of Neurology, Neurosurgery and Psychiatry 1994; 57: 419–425.

16. A M Saunders, W J Strittmatter, D Schmechel, P H St George-Hyslop, M A Pericak-Vance, S H Joo, B L Rosi, J F Gusella, D R Crapper-MacLachlan, M J Alberts, C Hulette, B Crain, D Goldgaber & A D Roses. Association of Apolipoprotein E allele E4 with late-onset familial and sporadic Alzheimer's disease. Neurology 1993; 43: 1467–1472.

17. E H Corder, A M Saunders, W J Strittmatter, D E Schmechel, P C Gaskell, G W Small, A D Roses, J L Haines, M A Pericak-Vance. Gene dose of Apolipoprotein E Type 4 Allele and the risk of Alzheimer's Disease in late onset families. Science, 1993; 261: 921.

18. E H Corder, A M Saunders, N J Riech, W J Strittmatter, D E Schmechel, P C Gaskell Jr., J B Rimmler, P A Locke, P M Connelly, K E Schmader, G W 1Small, A D Roses, J L Haines & M A Pericak-Vance. Protective effect of Apolipoprotein E2 allele decreases risk of late-onset Alzheimer's disease. Nature Genetics 1994; 7: 1–7.

19. C Talbot, C Lendon, N Craddock, S Shears, J C Morris, A Goate. Protection against Alzheimer's disease with ApoE E2. The Lancet 1994; 343: 1432–1433.

20. A M Saunders, K Schmader, C S Breitner, M D Benson, W T Brown, L Goldfarb, D Goldgaber, M G Manwaring, M H Szymanski, M McCown, K C Dole, D E Schmechel, W J Strittmatter, M A Pericak-Vance, A D Roses. Apolipoprotein E E4 allele distribution in late-onset Alzheimer's disease and in other amyloid-forming diseases. Neurology 1993; 342: 710–711.

21. J Poirier, J Davignon, D Bouthillier, S Kogan, P Bertrand, S Gauthier. Apolipoprotein E polymorphism and Alzheimer's disease. The Lancet 1993; 342: 697–699.

22. D S Borgaonkar, L C Schmidt, S E Martin, M D Kanzer, L Edelsohn, J Growdon, L A Farrer. Linkage of late-onset Alzheimer's disease with Apolipoprotein E4 on chromosome 19. The Lancet, 1993: 342: 625.

23. R Mayeux, Y Stern, R Ottman, T K Tatemichi, M-X Tang, G Maestre, B S Coleen Ngai, B Tyoko & H Ginsberg. The Apolipoprotein E4 allele in patients with Alzheimer's disease. American Neurological Association 1993; 34: 752–754.

24. Allen D Roses, Warren J Strittmatter, Margaret A Pericak-Vance, Elizabeth H Corder, Ann M Saunders, Donald E Schmechel. et al Lancet. Clinical application of apolipoprotein E genotyping to Alzheimer's diease. 1994; 343: 1564–1565.

25. Houlden H, Collinge J, Kennedy A, Newman S, Rossor M, Lannefelt L, Lilius L, Winblad B, Crook R, Duff K and Hardy J. ApoE genotype and Alzheimer's disease. Lancet 1993, 342, 737–738.

26. K Kervinen, M J Sovalainen, J Salokannel, A Hynninen, J Heikkinen, C Ehnholm, M J Koistinen, Y A Kesaniemi. Apolipoprotein E and B polymorphisms—longevity factors assessed in nonagenarians. Atherosclerosis 1994; 105: 89–95.

27. F Schachter, L Faure-Delanef, F Guenot, H Rouger, P Froguel, L Lesueur-Ginot & D Cohen. Genetic associations with human longevity at the ApoE and ACE loci. Nature Genetics 1994; 6: 29–32.

28. W J Strittmatter, K H Weisgraber, M Goedert, A M Saunders, D Huang, E H Corder, L-M Dong, R Jakes, M J Alberts, J R Gilbert, Seol-Heui Han, C Hulette, G Einstein, D E Schmechel, M A Pericak-Vance & A D Roses. Hypothesis: Microtuble instability and paired helical filament formation in the Alzheimer Disease brain are related to Apolipoprotein E genotype. Experimental Neurology 1994; 125: 163–171.

29. S C Waring, P C O-Brien, L T Kurland, S N Thibodeau, M-S Tsai, R C Petersen, C E Esteban-Santilan. Apoliopoprotein E allele in Chamoros with amyotrophic lateral sclerosis/parkinsonism-dementia complex. The Lancet, 1994; 343; 611.

30. J Hardy, R Crook, R Perry, R Raghavan & G W Roberts. ApoE genotype and Down's syndrome. The Lancet 1994; 343: 979–980.

31. H K Das, J McPherson; G A Bruns, S K Karathanasis , J L Breslow. Isolation, characterization and mapping to chromosome 19 of the human apolipoprotein E gene. J Biol. Chem. 1985; 260: 6240–6247.

32. J M Taylor, S Lauer, N Elshourbagy, C Reardon, E Taxman, D Walker, D Chang & Y K Paik. Structure and evolution of human Apolipoprotein genes: Identification of regulatory elements of the human Apolipoprotein E gene. Ciba Found. Symp. 1987; 130: 70–86.

33. E H Hixson and D T Vernier. Restriction isotyping of human apolipoprotein E by gene amplification and cleavage with HhaI. Journal of Lipid Research (1990) 31: 545–548.

34. Y Namba, Tomonaga M, Kawasaki H, Otomo E & Ikeda K. Apolipoprotein E immunoreactivity in cerebral deposits and neurofibrillary tangles in Alzheimer's disease. Brain Res. 541, 163–166 (1991).

35. W J Strittmatter et al. Apolipoprotein E—High avidity binding to β-amyloid and increased frequency of type 4 allele in late-onset familial Alzheimer's disease. Proc. Natn. Acad. Sci. U.S.A. 90, 1977–1981 (1993).

36. W J Strittmatter et al. Binding of human apolipoprotein E to synthetic amyloid β-peptide. Isoform specific effects and implications for late onset Alzheimer's disease. Proc. Natn. Acad. Sci. U.S.A. 90, 8098–8102 (1993).

37. J Ma, A Yee, B Brewer, S Das & H Potter. Amyloid-associated proteins αI antichymotrypsin and apolipoprotein E promote assembly of Alzheimer β-protein into filaments. Nature 372, 92–94 (1994).

38. P R Wenham, W H Price & G Blundell. Apolipoprotein E genotyping by one-stage PCR. Lancet 337, 1158–1159 (1991).

We claim:

1. A method of prognosing in a head-injured subject or a subject who may be at risk of sustaining a head injury for the likelihood that a head injury might give rise to a chronic neurodegenerative pathology which could result in neuropsychological, psychiatric or neurological deficits, the method comprising detecting, using an in vitro or ex vivo assay, the presence or absence of the ApoE isoform ApoE4 or of DNA encoding for the ApoE isoform ApoE4 in the subject, the presence of at least one ApoE4 allele being prognostic of increased risk for neuropsychological, psychiatric or neurological deficits in a head injured patient or one at risk of sustaining a head injury and the absence of an ApoE4 allele being prognostic of minimal increased risk for neuropsychological, psychiatric or neurological deficits.

2. A method according to claim 1 wherein said detection step involves collecting a sample of biological material containing DNA from the subject.

3. A method according to claim 2, wherein the biological sample is blood.

4. A method according to claim 1 wherein said detection step involves collecting a sample of biological material containing ApoE from the subject.

5. A method according to claim 4, wherein the biological sample is cerebrospinal fluid.

* * * * *